US009416354B1

(12) United States Patent
Liu

(10) Patent No.: US 9,416,354 B1
(45) Date of Patent: Aug. 16, 2016

(54) **FERULATE ESTERASE ISOLATED FROM *LACTOBACCILLUS FERMENTUM***

(71) Applicant: The United States of America, as represented by the Secretary of Agriculture, Washington, DC (US)

(72) Inventor: Siqing Liu, Dunlap, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/630,180

(22) Filed: Feb. 24, 2015

(51) Int. Cl.
| | |
|---|---|
| *C12N 9/18* | (2006.01) |
| *C12N 9/16* | (2006.01) |
| *C12N 9/14* | (2006.01) |
| *C12P 21/06* | (2006.01) |
| *C12P 19/34* | (2006.01) |
| *C12N 15/00* | (2006.01) |
| *C12N 1/20* | (2006.01) |
| *C07H 21/04* | (2006.01) |
| *C07K 1/00* | (2006.01) |

(52) U.S. Cl.
CPC ........... *C12N 9/18* (2013.01); *C12Y 301/01073* (2013.01)

(58) Field of Classification Search
CPC .......................... C12N 9/18; C12Y 301/01073
USPC ............ 435/197, 196, 195, 69.1, 91.1, 320.1, 435/252.3; 536/23.1, 23.2, 23.4; 530/350
See application file for complete search history.

(56) References Cited

PUBLICATIONS

Crepin, V.F. et al., "Functional classification of the microbial feruloyl esterases", (2004) Applied Microbiology Biotechnology 63:647-652.
Graf, Ernst, "Antioxidant Potential of Ferulic Acid", (1992) Free Radical Biology and Medicine 13:435-448.
Kabel, Mirjam A.et al., "Biochemical Characterization and Relative Expression Levels of Multiple Carbohydrate Esterases of the Xylanolytic Rumen Bacterium Prevotella ruminicola 23 Grown on an Ester-Enriched Substrate", (2011) Applied and Environmental Microbiololgy 77(16):5671-5681.
Kroon, Paul A. and Gary Williamson, "Hydroxycinnamates in plants and food: current and future perspectives", (1999) Journal of the Science of Food and Agriculture 79:355-361.
Lai, Kwan Kin et al., "Biochemical Properties of Two Cinnamoyl Esterases Purified from a Lactobacillus johnsonii Strain Isolated from Stool Samples of Diabetes-Resistant Rats" (2009) Applied and Environmental Microbiology 75 (15):5018-5024.
Liu, Siqing et al., "Cloning, Expression, Purification,and Analysis of Mannitol Dehydrogenase Gene mtlK from Lactobacillus brevis", (2005) Applied Biochemistry and Biotechnology vol. 121-124:391-401.
Liu, Siqing et al., "Metabolic engineering of a Lactobacillus plantarum double ldh knockout strain for enhanced ethanol production", (2006) Journal of Industrial Microbiology and Biotechnology 33:1-7.
MacKenzie, C. Roger et al., "Induction of Cellulolytic and Xylanolytic Enzyme Systems in *Streptomyces* spp.", (1987) Applied and Environmental Microbiology 53(12):2835-2839.
Rashamuse, K.J. et al., "A novel recombinant ethyl ferulate esterase from Burkholderia multivorans", (2007) Journal of Applied Microbiology 103:1610-1620.
Stewart, Jaclyn J. et al., "The Effects on Lignin Structure of Overexpression of Ferulate 5-Hydroxylase in Hybrid Poplar1[W]", (2009) Plant Physiology 150:621-635.
Szwajgier, Dominik et al., "The Use of a Novel Ferulic Acid Esterase from Lactobacillus acidophilus K1 for the Release of Phenolic Acids from Brewer's Spent Grain", (2010) Journal of the Institute of Brewing 116(3):293-303.
Szwajgier, Dominik and Anna Jakubczyk, "Production of Extracellular Ferulic Acid Esterases by Lactobacillus Strains Using Natural and Synthetic Carbon Sources", (2011) Acta Sci. Pol., Technol. Aliment. 10(3):287-302.
Topakas, Evangelos et al., "Microbial production, characterization and applications of feruloyl esterases", (2007) Process Biochemistry 42:497-509.
Crepin, V. F. et al., "Functional Classification of the Microbial Feruloyl Esterases", (2004) Appl Microbiol Biotechnol 63:647-652.
Graf, Ernest, "Antioxidant Potential of Ferulic Acid", (1992) Free Radical Biology & Medicine 13, pp. 435-448.
Kabel, Mirjam et al., "Biochemical Characterization and Relative Expression Levels of Multiple Carbohydrate Esterases of the Xylanolytic Rumen Bacterium Prevotella Ruminicola 23 Grown on an Ester-Enriched Substrate", Aug. 2011), Applied and Environmental Microbiology, 77(16): 5671-5681.
Kroon, Paul A. et al., "Hydroxycinnamates in Plants and Food: Current and Future Perspectives", (1999) Journal of Science of Food and Agriculture 79:355-361.
Lai, Kin Kwan et al., "Biochemical Properties of Two Cinnamoyl Esterases Purified From a Lactobacillus johnsonii Strain Isolated from Stool Samples of Diabetes-Resistant Rats", (Aug. 2009) Applied and Environmental Microbiology 75(15): 5018-5024.
Liu, Siqing et al., "Cloning, Expression, Purification, and Analysis of Mannitol Dehydrogenase Gene mtlK from Lactobacillus brevis", (2005) Applied Biochemistry and Biotechnology 121-124: 391-402.
Liu, Siqing et al., "Metabolic Engineering of a Lactobacillus Plantarum Double Idh Knockout Strain for Enhanced Ethanol Production" (2006) J Ind Microbiol Biotechnol 33:1-7.
MacKenzie, C. Roger et al., "Induction of Cellulolytic and Xylanolytic Enzyme Systems in *Streptomyces* spp.", (1987) Applied and Environmental Microbiolgy 53(12): 2835-2839.
Rashamuse, K.J. et al., "A Novel Recombinant Ethyl Ferulate Esterase from Burkholderia Multivorans", (2007) Journal of Applied Microbiology 103: 1610-1620.
Stewart, Jaclyn J. et al., "The Effects on Lignin Structure of Overexpression of Ferulate 5-Hydroxylase in Hybrid Poplar1[W]", (2009) Plant Physiology 150: 621-635 and Supplemental Material.
Szwajgier, Dominik et al., "The Use of a Novel Ferulic Acid Esterase from Lactobacillus Acidophilus K1 for the Release of Phenolic Acids from Brewer's Spent Grain", (2010) J. Inst. Brew. 116(3): 293-303.
Szwajgier, Dominik et al., "Production of Extracellular Ferulic Acid Esterases by Lactobacillus Strains Using Natural and Synthetic Carbon Sources", (2011) Acta Scientiarum Polonorum 10(3); 287-302.
Topakas, Evangelos et al., "Microbial Production, Characterization and Applications of Feruloyl Esterases", (2007) Process Biochemistry 42: 497-509.

*Primary Examiner* — Ganapathirama Raghu
(74) *Attorney, Agent, or Firm* — John D. Fado; David L. Marks

(57) ABSTRACT

The cDNA and amino acid sequences of a ferulate esterase obtained from *Lactobacillus fermentum* NRRL B-1932 is determined. An expression vector for expression of the ferulate esterase gene is generated. The recombinate ferulate esterase gene and transcribed protein contains a linker sequence and 6×HIS tag for purification. Enzymatic activity of the recombinant protein is determined.

11 Claims, 6 Drawing Sheets

| | | | | | | |
|---|---|---|---|---|---|---|
| 1932 | MEVAIKSAGL | TLRGLLEGSD | QVPNDRIAIL | MHGFKGDLGY | TEENLLNQLA | SEQ ID NO:5 |
| ATCC14931 | MEVAIKSAGL | TLRGLLEGSD | QVPNDRIAIL | MHGFKGDLGY | TEENLLNQLA | SEQ ID NO:7 |
| 3956FU | ----------GL | TLRGLLEGSN | QVPNDRIAIL | MHGFKGDLGY | TEENLLNQLA | SEQ ID NO:8 |
| | | | | | | |
| 1932 | HRLNDQGLAT | LRFDFAGCGK | SDGQFSDMTV | LSELQDGMKI | IDYARQEVQA | SEQ ID NO:5 |
| ATCC14931 | HRLNDQGLAT | LRFDFAGCGK | SDGQFSDMTV | LSELQDGMKI | IDYARQEVQA | SEQ ID NO:7 |
| 3956FU | HRLNDQGLAT | LRFDFAGCGK | SDGRFSDMTV | LSELQDGMKI | IDYARQEVQA | SEQ ID NO:8 |
| | | | | | | |
| 1932 | KEIILVGHSQ | GGVVASMLAA | YYRDVIDKLV | LLAPAATLKD | DALTGTCQGT | SEQ ID NO:5 |
| ATCC14931 | KEIILVGHSQ | GGVVASMLAA | YYRDVIDKLV | LLAPAATLKD | DALIGTCQGT | SEQ ID NO:7 |
| 3956FU | KEIILVGHSQ | GGVVASMLAA | YYRDVIDKLV | LLAPAATLKD | DALIGTCQGT | SEQ ID NO:8 |
| | | | | | | |
| 1932 | TYDPNHIPDY | VTVGGFKVGG | DYFRTAQLLP | IYKTAQHYAG | PVLMIHGLAD | SEQ ID NO:5 |
| ATCC14931 | TYDPNHIPDY | VTVGGFKVGG | DYFRTAQLLP | IYETAQHYAG | PVLMIHGLAD | SEQ ID NO:7 |
| 3956FU | TYDPNHIPDY | VTVGGFKVGG | DYFRTAQLLP | IYETAQHYAG | PVLMIHGLAD | SEQ ID NO:8 |
| | | | | | | |
| 1932 | TVVDPKASQK | YNVMYQNGVI | HFLEGASHQL | RGDGDQRETT | LQLVADFLN | SEQ ID NO:5 |
| ATCC14931 | TVVDPKASQK | YNVMYQNGVI | HFLEGASHQL | RGDGDQRETT | LQLVADFLN | SEQ ID NO:7 |
| 3956FU | TVVDPKASQK | YNVMYQNGVI | HFLEGASH--- | ---------- | --------- | SEQ ID NO:8 |

FIG. 2

SEQUENCE LISTING

```
<160> NUMBER OF SEQ ID NOS: 16

<210> SEQ ID NO 1
<211> LENGTH: 2168
<212> TYPE: DNA
<213> ORGANISM: Lactobacillus fermentum

<400> SEQUENCE: 1
taaccccggg gtagttatcg gagctatccc ccatcagggc cttcacatcg atgtattggc      60
gtggggtgac gcccagcttt tcttgcatgt atgccggggt gaactcctcg gtttgggtca     120
ccccgcgctt ggtaacggcc acggtggtgt ggtcggtggc cagctgggtc aaatcacggt     180
ccccggtcac aatcatcgtc tcaaagccgg cctggtcccc ttccttggcc agggtcccaa     240
tgatgtcatc ggcctcgtaa ttaactagtt cgtaagcgtg gaggccactt gcttcgacca     300
gcttgcgtac gtagggcagt tgttccacta gctcacccgg cgttttatca cggctcccct     360
tgtaatcggc gtacttttcg gtccgaaagg tggtcttacc ggcgtcaaag gccaccaagg     420
cggcgtctgg ttgaacctcc tttaatatgt gatccagcat cagtttgaac ccgtagatgg     480
ccgccgtgtg taacccgcc tggttggtaa acttctccat ctggttgtgc atggcgaaaa     540
acgcccggaa gacgatgcta ttcccgtcga ttaataaaag ctgcttagcc atttttatcc     600
gtccttcctt agtcactgct cccattgtag caaactttgc gccccgccgc ttgtccgccc     660
```

```
ccttaaataa agcgcttgcc atcgccttttt gacccgggta tcgtaaggat aaacatgaaa    720
gtgagttgat acaatggaag ttgcaatcaa gagtgccggt cttaccttac ggggggctgct    780 cgagggagc gaccaggtgc caaacgaccg gatcgccatt ttaatgcacg gttttaaggg     840
tgacctaggt tacaccgagg agaacctctt aaaccaactg gcccaccgct aaacgaccg     900 gggcctggcc acgttacggt ttgactttgc cggttgcggt aagtccgacg gtcagtttag    960
cgacatgacc gtgttaagcg aacttcaaga cggcatgaag atcatcgact acgcccgcca   1020
ggaggttcag gcaaaggaaa tcatcctggt tggccactca caaggcgggg tggtggcttc   1080
gatgctcgcc gcctactacc gcgacgtgat tgacaagtta gttctcttgg ccccagctgc   1140
caccctcaaa gatgacgccc tgatcgggac ttgccaagga accacctacg atcccaacca   1200
cattcccgac tacgtaacgg ttggtggctt taaagtcggc ggcgactact tcaggaccgc   1260
ccaactgcta ccaatttacg aaaccgccca gcactacgcc ggcccggttt tgatgatcca   1320
cggcctggcc gacacggtgg tcgacccaa ggcctcacaa aagtacaacg ttatgtacca    1380
aaacggggtg atccacttcc tggaggggc cagccaccag ttacgtggcg acggcgacca    1440
acgggaaacc acccttcaat tagtggccga tttcttaaac taacaaaaaa gaaccgcgct   1500
tttggcacgg ttcttttttg ttagtcgcgg ttgctcatcc caaagatttg caagagctgt   1560
aagaataagt taatgaagtc gaggtaaagc tgtaaggccc ccatgacggc caagccgccc   1620
atggaaactt cggccccgta gttaacgtag atggccttca tcttctgggc atcccaagcc   1680
gtttaagacc acgaagatga tcacggcgat gtaggagaag atgtaggtaa tcgctgctga   1740
gtgcaagaac atgttgatta agaagcgat gatcaaggcc accaacgccg ccatggcgtg    1800
gctaccggcc ttactgaggt cgcgcttggt gaccgtccca aagaccgcca tcgtcacgaa   1860
gatcacggcc gacgaaacga aggccgccgc aatgttggcc gccgtgtaca ttgccgagat   1920
caaggagaac tcaaccccgt agatgatcga caccaacatc aacatgataa aggaaccgac   1980
cggattcctg gtggcgctaa agctaatccc catcgaaagg gcgattggca agagcaaaat   2040
gatccagacc aagccggcat gcccagcaac aaaggtgaag accgccgctt tgaagacggt   2100
catggtcagg taggccgtaa tggccgagac gaagactgct aaagacatca acccgtacat   2160
ccgggtca                                                            2168
```

<210> SEQ ID NO 2
<211> LENGTH: 750
<212> TYPE: DNA
<213> ORGANISM: Lactobacillus fermentum

<400> SEQUENCE: 2

```
atggaagttg caatcaagag tgccggtctt accttacggg ggctgctcga ggggagcgac     60
caggtgccaa acgaccggat cgccatttta atgcacggtt ttaagggtga cctaggttac    120
accgaggaga acctcttaaa ccaactggcc caccgcttaa cgaccgggg cctggccacg     180 ttacggtttg actttgccgg ttgcggtaag tccgacggtc agtttagcga catgaccgtg    240
ttaagcgaac ttcaagacgg catgaagatc atcgactacg cccgccagga ggttcaggca    300
aaggaaatca tcctggttgg ccactcacaa ggcggggtgg tggcttcgat gctcgccgcc    360
tactaccgcg acgtgattga caagttagtt ctcttggccc cagctgccac cctcaaagat    420
gacgccctga tcgggacttg ccaaggaacc acctacgatc caaccacat tcccgactac     480 gtaacggttg gtggctttaa agtcggcggc gactacttca ggaccgccca actgctacca    540
atttacgaaa ccgcccagca ctacgccggc ccggttttga tgatccacgg cctggccgac    600
```

```
acggtggtcg accccaaggc ctcacaaaag tacaacgtta tgtaccaaaa cggggtgatc      660
cacttcctgg aggggccag ccaccagtta cgtggcgacg gcgaccaacg ggaaaccacc       720
cttcaattag tggccgattt cttaaactaa                                        750
```

<210> SEQ ID NO 3
<211> LENGTH: 21
<212> TYPE: DNA
<213> ORGANISM: Lactobacillus fermentum

<400> SEQUENCE: 3

```
agccattttt atccgtccct t                                                 21
```

<210> SEQ ID NO 4
<211> LENGTH: 21
<212> TYPE: DNA
<213> ORGANISM: Lactobacillus fermentum

<400> SEQUENCE: 4

```
gggggcctta cagctttacc t                                                 21
```

<210> SEQ ID NO 5
<211> LENGTH: 248
<212> TYPE: PRT
<213> ORGANISM: Lactobacillus fermentum

<400> SEQUENCE: 5

```
Met Glu Val Ala Ile Lys Ser Ala Gly Leu Thr Leu Arg Gly Leu Leu
 1               5                  10                  15

Glu Gly Ser Asp Gln Val Pro Asn Asp Arg Ile Ala Ile Leu Met His
            20                  25                  30

Gly Phe Lys Gly Asp Leu Gly Tyr Thr Glu Glu Asn Leu Leu Asn Gln
        35                  40                  45

Leu Ala His Arg Leu Asn Asp Gln Gly Leu Ala Thr Leu Arg Phe Asp
    50                  55                  60

Phe Ala Gly Cys Gly Lys Ser Asp Gly Gln Phe Ser Asp Met Thr Val
65                  70                  75                  80

Leu Ser Glu Leu Gln Asp Gly Met Lys Ile Ile Asp Tyr Ala Arg Gln
                85                  90                  95

Glu Val Gln Ala Lys Glu Ile Ile Leu Val Gly His Ser Gln Gly Gly
            100                 105                 110

Val Val Ala Ser Met Leu Ala Ala Tyr Tyr Arg Asp Val Ile Asp Lys
        115                 120                 125

Leu Val Leu Leu Ala Pro Ala Ala Thr Leu Lys Asp Asp Ala Leu Thr
    130                 135                 140

Gly Thr Cys Gln Gly Thr Thr Tyr Asp Pro Asn His Ile Pro Asp Tyr
145                 150                 155                 160

Val Thr Val Gly Gly Phe Lys Val Gly Gly Asp Tyr Phe Arg Thr Ala
                165                 170                 175

Gln Leu Leu Pro Ile Tyr Lys Thr Ala Gln His Tyr Ala Gly Pro Val
            180                 185                 190

Leu Met Ile His Gly Leu Ala Asp Thr Val Val Asp Pro Lys Ala Ser
        195                 200                 205

Gln Lys Tyr Asn Val Met Tyr Gln Asn Gly Val Ile His Phe Leu Glu
    210                 215                 220

Gly Ala Ser His Gln Leu Arg Gly Asp Gly Asp Gln Arg Glu Thr Thr
225                 230                 235                 240
```

Gln Leu Val Ala Asp Phe Leu Asn
            245

<210> SEQ ID NO 6
<211> LENGTH: 750
<212> TYPE: DNA
<213> ORGANISM: Lactobacillus fermentum

<400> SEQUENCE: 6

| | | |
|---|---|---|
| atggaagttg caatcaagag tgccggtctt accttacggg gctgctcga ggggagcgac | 60 |
| caggtgccaa acgaccggat cgccatttta atgcacggtt ttaagggtga cctaggctac | 120 |
| accgaggaga acctcttaaa ccaactggcc caccgcttaa acgaccaggg cctggccacg | 180 |
| ttacggtttg actttgccgg ttgcggtaag tccgacggtc agtttagcga catgaccgtg | 240 |
| ttaagcgaac ttcaagacgg catgaagatc atcgactacg cccgccagga ggttcaggca | 300 |
| aaggaaatca tcctggttgg ccactcacaa ggcggggtgg tggcttcgat gctcgccgcc | 360 |
| tactaccgcg acgtgattga caagttagtt ctcttggccc cagctgccac cctcaaagat | 420 |
| gacgccctga ccgggacttg ccaaggaacc acctacgatc caaccacat tcccgactac | 480 |
| gtaacggttg gtggcttcaa agtcggcggc gactacttca ggaccgccca actgctgcca | 540 |
| atttacaaaa ccgcccagca ctacgccggc ccggttttga tgatccacgg cctggccgac | 600 |
| acggtggtcg accccaaggc ctcacaaaag tacaacgtta tgtaccaaaa cggggtgatc | 660 |
| cacttcctgg aggggccag ccaccagtta cgtggcgacg gcgaccaacg ggaaaccacc | 720 |
| cttcaattag tggccgattt cttaaactaa | 750 |

<210> SEQ ID NO 7
<211> LENGTH: 249
<212> TYPE: PRT
<213> ORGANISM: Lactobacillus fermentum

<400> SEQUENCE: 7

Met Glu Val Ala Ile Lys Ser Ala Gly Leu Thr Leu Arg Gly Leu Leu
1               5                   10                  15

Glu Gly Ser Asp Gln Val Pro Asn Asp Arg Ile Ala Ile Leu Met His
            20                  25                  30

Gly Phe Lys Gly Asp Leu Gly Tyr Thr Glu Glu Asn Leu Leu Asn Gln
        35                  40                  45

Leu Ala His Arg Leu Asn Asp Gln Gly Leu Ala Thr Leu Arg Phe Asp
    50                  55                  60

Phe Ala Gly Cys Gly Lys Ser Asp Gly Gln Phe Ser Asp Met Thr Val
65                  70                  75                  80

Leu Ser Glu Leu Gln Asp Gly Met Lys Ile Ile Asp Tyr Ala Arg Gln
                85                  90                  95

Glu Val Gln Ala Lys Lys Ile Ile Leu Val Gly His Ser Gln Gly Gly
            100                 105                 110

Val Val Ala Ser Met Leu Ala Ala Tyr Tyr Arg Asp Val Ile Asp Lys
        115                 120                 125

Leu Val Leu Leu Ala Pro Ala Ala Thr Leu Lys Asp Asp Ala Leu Ile
    130                 135                 140

Gly Thr Cys Gln Gly Thr Thr Tyr Asp Pro Asn His Ile Pro Asp Tyr
145                 150                 155                 160

Val Thr Val Gly Gly Phe Lys Val Gly Gly Asp Tyr Phe Arg Thr Ala
                165                 170                 175

```
Gln Leu Leu Pro Ile Tyr Glu Thr Ala Gln His Tyr Ala Gly Pro Val
            180                 185                 190

Leu Met Ile His Gly Leu Ala Asp Thr Val Val Asp Pro Lys Ala Ser
        195                 200                 205

Gln Lys Tyr Asn Val Met Tyr Gln Asn Gly Val Ile His Phe Leu Glu
    210                 215                 220

Gly Ala Ser His Gln Leu Arg Gly Asp Gly Asp Gln Arg Glu Thr Thr
225                 230                 235                 240

Leu Gln Leu Val Ala Asp Phe Leu Asn
            245

<210> SEQ ID NO 8
<211> LENGTH: 249
<212> TYPE: PRT
<213> ORGANISM: Lactobacillus fermentum

<400> SEQUENCE: 8

Met Glu Val Ala Ile Lys Ser Ala Gly Leu Thr Leu Arg Gly Leu Leu
1               5                   10                  15

Glu Gly Ser Asn Gln Val Pro Asn Asp Arg Ile Ala Ile Leu Met His
            20                  25                  30

Gly Phe Lys Gly Asp Leu Gly Tyr Thr Glu Glu Asn Leu Leu Asn Gln
        35                  40                  45

Leu Ala His Arg Leu Asn Asp Gln Gly Leu Ala Thr Leu Arg Phe Asp
    50                  55                  60

Phe Ala Gly Cys Gly Lys Ser Asp Gly Arg Phe Ser Asp Met Thr Val
65                  70                  75                  80

Leu Ser Glu Leu Gln Asp Gly Met Lys Ile Ile Asp Tyr Ala Arg Gln
            85                  90                  95

Glu Val Gln Ala Lys Glu Ile Ile Leu Val Gly His Ser Gln Gly Gly
            100                 105                 110

Val Val Ala Ser Met Leu Ala Ala Tyr Tyr Arg Asp Val Ile Asp Lys
        115                 120                 125

Leu Val Leu Leu Ala Pro Ala Ala Thr Leu Lys Asp Asp Ala Leu Ile
    130                 135                 140

Gly Thr Cys Gln Gly Thr Thr Tyr Asp Pro Asn His Ile Pro Asp Tyr
145                 150                 155                 160

Val Thr Val Gly Gly Phe Lys Val Gly Gly Asp Tyr Phe Arg Thr Ala
            165                 170                 175

Gln Leu Leu Pro Ile Tyr Glu Thr Ala Gln His Tyr Ala Gly Pro Val
            180                 185                 190

Leu Met Ile His Gly Leu Ala Asp Thr Val Val Asp Pro Lys Ala Ser
        195                 200                 205

Gln Lys Tyr Asn Val Met Tyr Gln Asn Gly Val Ile His Phe Leu Glu
    210                 215                 220

Gly Ala Ser His Gln Leu Arg Gly Asp Gly Asp Gln Arg Glu Thr Thr
225                 230                 235                 240

Leu Gln Leu Val Ala Asp Phe Leu Asn
            245

<210> SEQ ID NO 9
<211> LENGTH: 26
<212> TYPE: DNA
<213> ORGANISM: Artificial Sequence
<220> FEATURE:
<223> OTHER INFORMATION: primer
```

<400> SEQUENCE: 9
catgaaagtg agttgatacc atgga                                    26

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
tcggatcccg gtttaagaaa tc                                       22

<210> SEQ ID NO 11
<211> LENGTH: 22
<212> TYPE: PRT
<213> ORGANISM: Artificial Sequence
<220> FEATURE:
<223> OTHER INFORMATION: linker

<400> SEQUENCE: 11

Arg Asp Pro Asn Ser Ser Ser Val Asp Lys Leu Ala Ala Ala Leu Glu
1               5                   10                  15

His His His His His His
            20

<210> SEQ ID NO 12
<211> LENGTH: 270
<212> TYPE: PRT
<213> ORGANISM: Artificial Sequence
<220> FEATURE:
<223> OTHER INFORMATION: chimeric protein

<400> SEQUENCE: 12

Met Glu Val Ala Ile Lys Ser Ala Gly Leu Thr Leu Arg Gly Leu Leu
1               5                   10                  15

Glu Gly Ser Asp Gln Val Pro Asn Asp Arg Ile Ala Ile Leu Met His
            20                  25                  30

Gly Phe Lys Gly Asp Leu Gly Tyr Thr Glu Glu Asn Leu Leu Asn Gln
        35                  40                  45

Leu Ala His Arg Leu Asn Asp Gln Gly Leu Ala Thr Leu Arg Phe Asp
    50                  55                  60

Phe Ala Gly Cys Gly Lys Ser Asp Gly Gln Phe Ser Asp Met Thr Val
65                  70                  75                  80

Leu Ser Glu Leu Gln Asp Gly Met Lys Ile Ile Asp Tyr Ala Arg Gln
                85                  90                  95

Glu Val Gln Ala Lys Glu Ile Ile Leu Val Gly His Ser Gln Gly Gly
            100                 105                 110

Val Val Ala Ser Met Leu Ala Ala Tyr Tyr Arg Asp Val Ile Asp Lys
        115                 120                 125

Leu Val Leu Leu Ala Pro Ala Ala Thr Leu Lys Asp Asp Ala Leu Thr
    130                 135                 140

Gly Thr Cys Gln Gly Thr Thr Tyr Asp Pro Asn His Ile Pro Asp Tyr
145                 150                 155                 160

Val Thr Val Gly Gly Phe Lys Val Gly Asp Tyr Phe Arg Thr Ala
                165                 170                 175

Gln Leu Leu Pro Ile Tyr Lys Thr Ala Gln His Tyr Ala Gly Pro Val
            180                 185                 190

Leu Met Ile His Gly Leu Ala Asp Thr Val Val Asp Pro Lys Ala Ser 195                 200                 205
Gln Lys Tyr Asn Val Met Tyr Gln Asn Gly Val Ile His Phe Leu Glu
        210                 215                 220

Gly Ala Ser His Gln Leu Arg Gly Asp Gly Asp Gln Arg Glu Thr Thr
225                 230                 235                 240

Gln Leu Val Ala Asp Phe Leu Asn Arg Asp Pro Asn Ser Ser Ser Val
                245                 250                 255

Asp Lys Leu Ala Ala Ala Leu Glu His His His His His His
        260                 265                 270

<210> SEQ ID NO 13
<211> LENGTH: 816
<212> TYPE: DNA
<213> ORGANISM: Artificial Sequence
<220> FEATURE:
<223> OTHER INFORMATION: coding sequence for chimeric protein

<400> SEQUENCE: 13
atggaagttg caatcaagag tgccggtctt accttacggg ggctgctcga ggggagcgac      60
caggtgccaa cgaccggat cgccatttta atgcacggtt ttaagggtga cctaggctac     120
accgaggaga acctcttaaa ccaactggcc caccgcttaa cgaccaggg cctggccacg     180 ttacggtttg actttgccgg ttgcggtaag tccgacggtc agtttagcga catgaccgtg     240
ttaagcgaac ttcaagacgg catgaagatc atcgactacg cccgccagga ggttcaggca     300
aaggaaatca tcctggttgg ccactcacaa ggcgggtgg tggcttcgat gctcgccgcc     360
tactaccgcg acgtgattga caagttagtt ctcttggccc cagctgccac cctcaaagat     420
gacgccctga ccgggacttg ccaaggaacc acctacgatc caaccacat tcccgactac     480 gtaacggttg gtggcttcaa agtcggcggc gactacttca ggaccgccca actgctgcca     540
atttacaaaa ccgcccagca ctacgccggc ccggttttga tgatccacgg cctggccgac     600
acggtggtcg accccaaggc ctcacaaaag tacaacgtta tgtaccaaaa cggggtgatc     660
cacttcctgg aggggccag ccaccagtta cgtggcgacg gcgaccaacg ggaaaccacc     720
cttcaattag tggccgattt cttaaaccgg gatccgaatt cgagctccgt cgacaagctt     780
gcggccgcac tcgagcacca ccaccaccac cactga                              816

<210> SEQ ID NO 14
<211> LENGTH: 16
<212> TYPE: PRT
<213> ORGANISM: Artificial Sequence
<220> FEATURE:
<223> OTHER INFORMATION: linker

<400> SEQUENCE: 14

Arg Asp Pro Asn Ser Ser Ser Val Asp Lys Leu Ala Ala Ala Leu Glu
1               5                   10                  15

<210> SEQ ID NO 15
<211> LENGTH: 6
<212> TYPE: PRT
<213> ORGANISM: Artificial Sequence
<220> FEATURE:
<223> OTHER INFORMATION: HIS tag

<400> SEQUENCE: 15

His His His His His His
1               5

```
<210> SEQ ID NO 16
<211> LENGTH: 8
<212> TYPE: PRT
<213> ORGANISM: Artificial Sequence
<220> FEATURE:
<223> OTHER INFORMATION: FLAG tag

<400> SEQUENCE: 16

Asp Tyr Lys Asp Asp Asp Asp Lys
1               5
```

FERULATE ESTERASE ISOLATED FROM *LACTOBACCILLUS FERMENTUM*

BACKGROUND OF INVENTION

1. Field of Invention

This invention relates to a novel ferulate esterase isolated from *Lactobacillus fermentum*, the amino acid and cDNA sequences of this novel ferulate esterase and its use in fermentation.

2. Description of the Prior Art

Lignocellulosic biomass materials are renewable, abundant and sustainable. In the most recent decade, lignocellulosic materials have been envisioned to replace petroleum resources for production of fuels and chemicals. Research focused on conversion of lignocellulosic materials to fuels and chemicals has become a global priority because of the limited petroleum supply. Based on chemical composition, lignocellulosic biomass contains three major polymers; cellulose (35-50%), hemicellulose (20-35%), and lignin (10-20%). Cellulose and hemicelluloses are covalently bounded through ester linkages to lignin via variety of hydroxycinnamic acids including ferulic, p-coumaric, sinapic and p-cafferic acid. The tight ester-ether bridges among the polysaccharides form the interwoven mesh-like plant cell wall structure that supports plant growth and development (Kroon and Williamson, *J. Science of Food and Agriculture* 79(3): 355-361 (1999)). In nature, when plants die, these polymers and ester bridges are usually degraded and broken down slowly by complicated orchestrated action of cellulases, hemicellulases and other specific enzymes including ferulic acid esterases that are produced by microbes under suitable anaerobic environmental conditions.

Feruloyl esterase catalyzes the hydrolysis of the 4-hydroxy-3-methoxycinnamoyl (feruloyl) group from an esterified sugar, resulting in the cleavage of the ester cross linkages. See MacKenzie, et al., *Appl. Environ. Microbiol.*, 53(12): 2835-2839 (1987); Rashamuse, et al., *J. Applied Microbio.*, 103(5):1610-1620 (2007); and Kabel, et al., *Appl. Environ. Microbiol.*, 77(16):5671-5681 (2011). These microbial ferulate esterases are also referred to hemicellulase accessory enzymes, because they are required to work together with xylanases and pectinases in degrading hemicelluloses of plant cell wall.

Ferulic acid esterases break down ester bonds between hydroxycinnamates and sugar (Crepin, et al., *Appl. Microbiol. Biotech.*, 63(6):647-652 (2004); Topakas, et al., *Process Biochemistry*, 42(4):497-509 (2007); and Stewart, et al., *Plant Physiology*, 150(2):621-635 (2009)). The production of feruloyl esterase activities can be detected on agar plate such as MRS-ethyl ferulate plate, in which the main carbon source is substituted with 1% ethyl ferulate. The hydrolysis of ethyl ferulate by feruloyl esterase can be visualized as clear zones around the individual colonies. (Kin, et al., *Appl. Environ. Microbiol.*, 75(15):5018-5024 (2009)). A number of *Bacillus* spp. predominantly *B. subtilis* strains, exhibit feruloyl esterase activity by this method. Of the examined lactobacilli, *Lactobacillus fermentum* (NCFB 1751) shows the highest level of ferulic acid esterase activity. The enzyme is released from harvested cells by sonication and has pH and temperature optima of 6.5 and 30° C. respectively. (Szwajgier, et al., *J. Instit. Brewing*, 116(3):293-303 (2010); Szwajgier and Jakubczyk, *Acta Scientiarum Polonorum, Technologia Alimentaria*, 10(3):287-302 (2011)). Biochemical characterization and relative expression levels of multiple carbohydrate esterases of the xylanolytic rumen bacterium *Prevotella ruminicola* 23 grown on an ester-enriched substrate has been performed (Kabel, et al. (2011)).

Because of the essential role ferulate esterase plays during biomass degradation and its use in the production of ferulic acid which is used in foods and in skin care products because of its antioxidant properties (see, Graf, E. *Free Radic. Biol. Med.* 13:435-448 (1992), it is useful to identify the cDNA and amino acid sequence of a highly active ferulate esterase and to express the highly active ferulate esterase in a heterologous bacteria and purify the enzyme.

BRIEF DESCRIPTION OF THE INVENTION

It is an object of this invention to have a novel ferulate esterase having optimal enzymatic activity at pH 6.5 and 37° C. This novel ferulate esterase is produced by *Lactobacillus fermentum* NRRL B-1932. It is another object of this invention to have a cDNA for this novel ferulate esterase which is in SEQ ID NO: 6. It is a further object of this invention that this novel ferulate esterase has an amino acid sequence of SEQ ID NO: 5. It is an object of this invention to have an expression vector containing the DNA sequence of this novel ferulate esterase (SEQ ID NO: 6) operably linked to a promoter. It is another object of this invention to have a recombinant bacteria containing this expression vector which contains the DNA sequence of this novel ferulate esterase (SEQ ID NO: 6) operably linked to a promoter, where the recombinant bacteria is not *L. fermentum* NRRL B-1932, or more generally, *L. fermentum*.

It is an object of this invention to have a novel ferulate esterase having optimal enzymatic activity at pH 6.5 and 37° C. This novel ferulate esterase is produced by *Lactobacillus fermentum* NRRL B-1932 and has the amino acid sequence of SEQ ID NO: 5. It is an object of this invention to have an expression vector containing a DNA sequence that encodes this novel ferulate esterase which has the amino acid sequence of SEQ ID NO: 5, where the DNA sequence is operably linked to a promoter. It is another object of this invention to have a recombinant bacteria containing this expression vector which contains a DNA sequence encoding this novel ferulate esterase (SEQ ID NO: 6) operably linked to a promoter, where the recombinant bacteria is not *L. fermentum* NRRL B-1932, or more generally, *L. fermentum*.

It is another object of this invention to have a chimeric protein which contains a first section having ferulate esterase activity, a second section for purification of the chimeric protein, and optionally a third section for separating the ferulate esterase activity section from the purification section. It is another object of this invention that the ferulate esterase activity section of the chimeric protein has the amino acid sequence of SEQ ID NO: 5. It is another object of this invention to have an expression vector containing a promoter and a DNA sequence which encodes this chimeric protein such that the promoter is operably linked to the DNA sequence encoding the chimeric protein. It is a further object of this invention to have a recombinant bacterium that contains this expression vector and produces the chimeric protein. This chimeric protein as optimal enzymatic activity at pH 6.5 and 37° C. In one embodiment of this invention the purification section and the linker section have the amino acid sequence of SEQ ID NO: 11.

It is another object of this invention to have a chimeric protein which contains a first section having ferulate esterase activity, a second section for purification of the chimeric protein, and a third section for separating the ferulate esterase activity section from the purification section. It is another object of this invention that the chimeric protein has the amino acid sequence of SEQ ID NO: 12. It is another object of this invention to have an expression vector containing a promoter operably linked to a DNA sequence which encodes this chimeric protein. It is a further object of this invention to have a recombinant bacterium that contains this expression vector and produces the chimeric protein. This chimeric protein as optimal enzymatic activity at pH 6.5 and 37° C.

BRIEF DESCRIPTION OF THE FIGURES

FIG. 2 shows the amino acid sequence alignment of three known ferulate esterase proteins from *L. fermentum* NRRL B-1932 (SEQ ID NO: 5), *L. fermentum* ATCC14931 (Genbank ZP_03945661.1) (SEQ ID NO: 7), and *L. fermentum* 3956FU (Genbank YP_001844134) (SEQ ID NO: 8). Non-identical amino acids are indicated in bold text at amino acids 20, 74, 144, and 193 based on the sequence of ferulate esterase from *L. fermentum* NRRL B-1932.

DETAILED DESCRIPTION OF THE INVENTION

Figure 1:
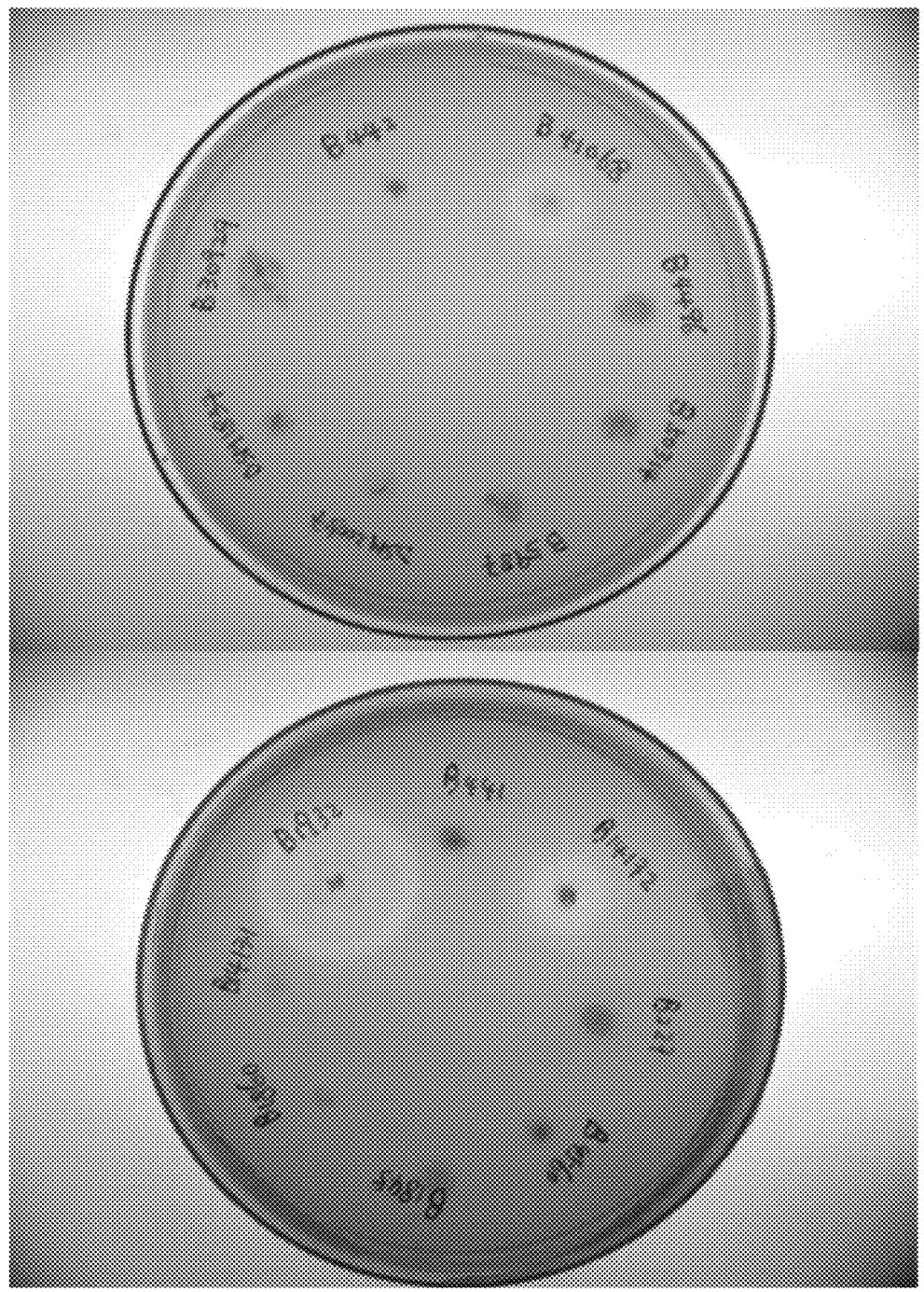
FIG. 1 shows two MRS-EHM plate assays detecting ferulate esterase activity from sixteen isolated bacterial colonies mentioned in Table 2. Each indicated bacterium strain is inoculated in one spot. The bacteria strains that produced and secreted ferulate esterase break down EHM (ethyl-4-hydroxy-3 methoxycinnamate) on the plate and form halo rings. The diameters of the halo ring are indicative of the relative strength of enzymatic activity.

This invention involves the identification of a bacterial strain that produces highly active ferulate esterase, the isolation and characterization of the cDNA sequence of the gene encoding the ferulate esterase, the isolation and characterization of the ferulate esterase including its amino acid sequence, and the transformation of a heterologous bacteria with an expression vector containing the cDNA sequence of the ferulate esterase operably linked to a promoter, and the isolation and purification of the expressed ferulate esterase. This invention also involves a chimeric protein having ferulate esterase activity. This chimeric protein has a first section containing the amino acids which have ferulate esterase activity, a second section containing a tag for purifying the chimeric protein, and a third section containing a linker sequence to separate the first section from the second section. This invention also involves the DNA sequence of the chimeric protein and an expression vector containing that DNA sequence operably linked to a promoter. Recombinant bacteria containing the expression vector encoding the chimeric protein are also included in the invention.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in gel after being subjected to electrophoresis. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in daltons (Da), kilodaltons (kDa) or amino acid residue numbers. Proteins sizes are estimated from gel electrophoresis, from sequenced proteins, from derived amino acid sequences, or from published protein sequences.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98(1994)).

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 1 provides a list of exemplary conservative amino acid substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

TABLE 1

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gla, Glu |
| Ile | Leu, Val |
| Leu | Ile, Val |
| Lys | Arg, Gln, Glu |
| Met | Leu, Ile |
| Phe | His, Met, Ley, Trp, Tyr |
| Ser | Cys, Thr |
| Thr | Ser, Val |
| Trp | Phe, Tyr |
| Tyr | His, Phe, Trp |
| Val | Ile, Leu, Thr |

As contemplated herein, a polypeptide, protein, or peptide may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation), hydroxylation, iodination (e.g., of thyroid hormones), and phosphorylation (e.g., the addition of a phosphate group, usually to serine, tyrosine, threonine or histidine) are possible.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", and "transfection" are similar in meaning to "recombinant". "Transformation", "transgenic", and "transfection" refer to the transfer of a polynucleotide into the genome of a host organism (including a virus) or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of transferred polynucleotide in order for the transgenic organism or cell to live and/or grow. Polynucleotides that are transformed into a cell but are not integrated into the host's chromosome remain as an expression vector within the cell. One may need to grow the cell under certain conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

An expression vector or simply a "vector", as used herein, refers to nucleic acid capable of replicating in a selected host cell or organism. An expression vector can replicate as an autonomous structure, or alternatively can integrate into the host cell chromosomes or the nucleic acids of an organelle, and thus replicate along with the host cell genome. Thus, an expression vector contains polynucleotides capable of replicating in a selected host cell, organelle, or organism, e.g., a plasmid, virus, artificial chromosome, nucleic acid fragment, and for which certain genes on the expression vector are transcribed and translated into a polypeptide or protein within the cell, organelle or organism; or any suitable construct known in the art, which comprises an "expression cassette". An expression vector for this invention contains the DNA of interest (the cDNA encoding the ferulate esterase described herein, with or without the linker sequence and 6×HIS tag) operably linked to a promoter. A polynucleotide sequence is operably linked to an expression control sequence(s) (e.g., a promoter and, optionally, an enhancer) when the expression control sequence controls and regulates the transcription and translation of that polynucleotide sequence. An expression vector is a replicon, such as plasmid, phage or cosmid, and which contains the desired polynucleotide sequence operably linked to the expression control sequence(s). The promoter may be similar or identical to a viral, phage, bacterial, yeast, insect, plant, or mammalian promoter. Similarly, the enhancer may be the sequences of an enhancer from virus, phage, bacteria, yeast, insects, plants, or mammals.

The term "operably linked" refers to the association of two or more nucleic acid fragments on a single polynucleotide so that the function of one is affected by the other. For example, a promoter is operably linked with a coding sequence so that the promoter is capable of affecting the expression of that coding sequence (i.e., that the coding sequence is under the transcriptional control of the promoter). Coding sequences can be operably linked to regulatory sequences in sense or antisense orientation. When a promoter is operably linked to a polynucleotide sequence encoding a protein or polypeptide, the polynucleotide sequence should have an appropriate start signal (e.g., ATG) in front of the polynucleotide sequence to be expressed. Further, the sequences should be in the correct reading frame to permit transcription of the polynucleotide sequence under the control of the expression control sequence and, translation of the desired polypeptide or protein encoded by the polynucleotide sequence. If a gene or polynucleotide sequence that one wants to insert into an expression vector does not contain an appropriate start signal, such a start signal can be inserted in front of the gene or polynucleotide sequence. In addition, a promoter can be operably linked to a RNA gene encoding a functional RNA.

A "promoter" is an expression control sequence and is capable of controlling the expression of a coding sequence or functional RNA. In general, a coding sequence is located 3' to a promoter sequence. The promoter sequence comprises of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even synthetic nucleotide segments. It is understood by those skilled in the art that different promoters may direct the expression of a gene in different tissues or cell types, or at different stages of development, or in response to different environmental conditions. Promoters that cause a polynucleotide to be expressed in most cell types at most times are commonly referred to as "constitutive promoters". "Inducible promoters" are promoters that cause a polynucleotide to be expressed under specific conditions such as, but not limited to, in specific tissue, at specific stages of development, or in response to specific environmental conditions, e.g., wounding of tissue or presence or absence of a particular compound. It is further recognized that because in most cases the exact boundaries of regulatory sequences have not been completely defined, nucleic acid fragments of different lengths may have identical promoter activity. In addition, promoters for bacteria are well-known to of ordinary skill in the art. For example, examples of bacterial promoters include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus* spp., the int promoter of bacteriophage lambda, the bla promoter of pBR322, and the CAT promoter of the chloramphenicol acetyl transferase gene. Prokaryotic promoters have been reviewed by Glick, *Ind. Microbiol.* 1:277 (1987), Watson, et al., *Molecular Biology of the Gene,* 4$^{th}$ ed. (Benjamin Cummins 1987), and by Ausubel, et al. (1994).

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

This invention utilizes routine techniques in the field of molecular biology. Basic texts disclosing the general methods of use in this invention include Green and Sambrook, *Molecular Cloning—A Laboratory Manual* 4th ed. 2012, Cold Spring Harbor Laboratory; Kriegler, *Gene Transfer and Expression: A Laboratory Manual* (1993); and Ausubel et al., eds., *Current Protocols in Molecular Biology,* 1994-current, John Wiley & Sons. Unless otherwise noted, technical terms are used according to conventional usage. Definitions of common terms in molecular biology maybe found in e.g., Benjamin Lewin, *Genes IX,* published by Oxford University Press, 2007 (ISBN 0763740632); Krebs, et al. (eds.), *The Encyclopedia of Molecular Biology,* published by Blackwell Science Ltd., 1994 (ISBN 0-632-02182-9); and Robert A. Meyers (ed.), *Molecular Biology and Biotechnology: a Comprehensive Desk Reference,* published by VCH Publishers, Inc., 1995 (ISBN 1-56081-569-8).

The examples below describe a chimeric protein having the following three sections: a ferulate esterase activity section (first section), a purification section (second section), and a separation section (third section). The linker section is optional. In the examples below, the linker section contains the sixteen amino acids in SEQ ID NO: 14. Of course, one of ordinary skill in the art knows of many different sets of amino acids that can be used as the linker (the separation section). The ferulate esterase activity section (first section) can have the amino acid sequence of SEQ ID NO: 5 for the ferulate esterase protein from *L. fermentum* NRRL B-1932. Alternatively, the amino acid sequence of the ferulate esterase activity section (first section) can be modified slightly for the chimeric protein, as in the examples below. In the examples below, the purification section (second section) contains a tag of six histidine amino acids (SEQ ID NO: 15). Of course, one of ordinary skill in the art knows of other amino acid sequences that can be used to facilitate the purification of the chimeric protein. See discussion below.

In the examples below, the chimeric protein is encoded by a DNA sequence (SEQ ID NO: 13) in which the DNA sequence of the ferulate esterase section differs slightly from the DNA sequence encoding ferulate esterase isolated from *L. fermentum* NRRL B-1932 (SEQ ID NO: 6). This invention also involves an expression vector which contains a promoter operably linked to the DNA sequence encoding the chimeric protein described herein. In the examples below, in the chimeric protein, the first section (having ferulate esterase activity) is attached to 6×HIS tag (the second section for purifying the chimeric protein) (SEQ ID NO: 15) via a 16 amino acid linker (SEQ ID NO: 14). The DNA sequence encoding this chimeric protein is operably linked to an IPTG-inducible promoter in the expression vector. This expression vector is used to transform *Escherichia coli* for production of the chimeric protein having ferulate esterase activity. One of ordinary skill in the art understands that and knows of many different types of expression vectors that can be used and is knowledgeable of these expression vectors. As discussed above, one of ordinary skill of the art is aware of and knowledgeable about other types of inducible promoters and constitutive promoters that may be used in the expression vector to cause transcription of mRNA encoding the chimeric protein having ferulate esterase activity. One of ordinary skill in the art also is aware and knowledgeable of other linker sequences (separation section) that could be used to separate the ferulate esterase section of the chimeric protein from the tag (purification section). Furthermore, one of ordinary skill in the art is familiar with other tags (purification sections) which can be used to purify the chimeric protein. Non-limiting examples of such tags include, but are not limited to, glutathione S-transferase tag (GST), maltose-binding protein, and FLAG (an 8-amino acid peptide of Asp-Tyr-Lys-Asp-Asp-Asp-Asp-Lys (SEQ ID NO: 16) in the pFLAG expression vector). Furthermore, one of ordinary skill in the art is aware and knowledgeable about other bacteria that could be transformed with the desired expression vector and produce the ferulate esterase protein. Non-limiting examples of such bacteria include *Bacillus subtilis*, *B. megaterium*, *Lactococcus lactis*, and *Lactobacillus platarum*. *Lactobacillus fermentum* NRRL B-1932 in particular is not used to produce ferulate esterase with a DNA sequence of SEQ ID NO: 6 or amino acid sequence of SEQ ID NO: 5 from an expression vector. However, recombinant *L. fermentum* NRRL B-1932 transformed with an expression vector encoding the chimeric protein having ferulate esterase activity can be used to produce the chimeric protein because the chimeric protein is not normally produced by *L. fermentum* NRRL B-1932.

It is anticipated that the purified ferulate esterase by itself or as part of a chimeric protein can be combined with other enzymes for degradation of lignocellulosic materials. *Lactobacillus* esterases (with GRAS status) are used to improve the texture and/or flavor of fermented foods. As such, the purified ferulate esterase and/or chimeric protein having ferulate esterase activity described herein can also be used to help improve the texture and/or flavor of fermented food by partially digesting plant cell walls to produce a desired functional food. The purified ferulate esterase and/or chimeric protein having ferulate esterase activity described herein can also be used to produce ferulic acid. Ferulic acid can promote insulin production, and thus may prevent diabetes. See, Balasubashini, et al., *Acta Diabetol.* 40:118-122 (2003). Ferulic acid can also prevent oxidative stress and lipid peroxidation. See, Srinivasan, et al., *J. Clin. Biochem. Nutr.* 40:92-100 (2007); Guglielmetti, et al., *AEM* 74:1284-1288 (2008); and Balasubashini, et al., *Phytother. Res.* 18:310-314 (2004).

Having now generally described this invention, the same will be better understood by reference to certain specific examples and drawings, which are included herein only to further illustrate one embodiment of the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1

Identification of a *Lactobacillus* Containing Strong Ferulate Esterase Activity To identify a bacteria containing strong ferulate esterase activity, thirty-three different *Lactobacillus* strains listed in Table 2, infra, are obtained from ATCC, DSM and NRRL public culture collections. *Lactobacillus plantarum* NCIMB 8826 is obtained from National Collections of Industrial and Marine Bacteria Ltd., Aberdeen, Scotland, and *Lactobacillus casei* CRL 686 is obtained from the Centro de Referencia para Lactobacilos. The bacteria are maintained on MRS plates (Becton Dickinson, Sparks, Md.) under anaerobic conditions (BBL GasPak anaerobic system, Becton Dickinson, Franklin Lakes, N.J.) and grown in MRS broth at 37° C. without shaking. See Liu, et al., *Appl. Biochem. Biotechnol.* 121-124: 391-401 (2005); and Liu, et al., *J. Ind. Microbiol. Biotechnol.* 33(1):1-7 (2006).

TABLE 2

| Bacterial strains | EHM Activity | Clearing Zone Diameters |
| --- | --- | --- |
| *Lactobacillus amylophilis* NRRL B-4437 | yes | 9 mm |
| *Lactobacillus amylovorus* NRRL B-4540 | yes | 22 mm |
| *Lactobacillus brevis* ATCC 367 | No | |
| *Lactobacillus brevis* NRRL B-3065 | No | |
| *Lactobacillus buchneri* NRRL B-1837 | No | |
| *Lactobacillus buchneri* NRRL B-1860 | No | |
| *Lactobacillus buchneri* NRRL B-1862 | No | |
| *Lactobacillus buchneri* NRRL B-30929 | No | |
| *Lactobacillus buchneri* DSM 5987 | No | |
| *Lactobacillus buchneri* DSM 20057 | No | |
| *Lactobacillus casei* ATCC 334 | no | |
| *Lactobacillus casei* ATTC 11578 | no | |
| *Lactobacillus casei* ATTC 4646 | yes | 8 mm |
| *Lactobacillus casei* CRL 686 | yes | 13 mm |
| *Lactobacillus casei* NRRL B-1922 | yes | 10 mm |
| *Lactobacillus casei* NRRL B-441 | no | |
| *Lactobacillus crisptus* NRRL B-4391 | yes | 4 mm |
| *Lactobacillus delbrueckii* DSM 20074 | no | |
| *Lactobacillus fermentum* NRRL B-3693 | yes | 17 mm |
| *Lactobacillus fermentum* NRRL B-1840 | yes | 20 mm |
| *Lactobacillus fermentum* NRRL B-1932 | yes | 38 mm |
| *Lactobacillus johnsonii* NRRL B-2178 | yes | 21 mm |
| *Lactobacillus malefermentans* NRRL B-1861 | no | |
| *Lactobacillus mucosae* NRRL B-41068 | yes | 18 mm |
| *Lactobacillus paracasei* NRRL B-50314 | no | |
| *Lactobacillus paracasei* NRRL B-4560 | no | |
| *Lactobacillus paracollinoides* NRRL B-1845 | no | |
| *Lactobacillus pentosus* NRRL B-227 | no | |
| *Lactobacillus plantarum* NCIMB 8826 | no | |
| *Lactobacillus plantarum* NRRL B-4496 | no | |
| *Lactobacillus rhamnosus* NRRL B-442 | no | |
| *Lactobacillus reuteri* NRRL B-14171 | no | |
| *Lactobacillus reuteri* NRRL B-14172 | yes | 19 mm |

The thirty-three different strains of *Lactobacillus* are inoculated on MRS without glucose plates, and incubated overnight at 37° C. A well-isolated single colony from each MRS plate is transferred onto MRS-EHM plates (MRS with ethyl-4-hydroxy-3-methoxycinnamate) and incubated at 37° C. for 72 hours. The MRS-EHM plates are made by adding 7.5 g agar to 500 ml MRS minus glucose media. MRS minus glucose media contains the following per liter: 5 g of casamino acids, 5 g of peptone, 5 g of yeast extract, 0.5 ml of Tween 80, 0.05 g of $MnSO_4 \cdot 4H_2O$, 0.2 g of $MgSO_4 \cdot 7H_2O$, 0.1 g of $CoCl_2 \cdot 6H_2O$, and 5 g of sodium acetate. The pH of the media is adjusted to 6.5. This mixture was sterilized by autoclave, and then allowed to cool down to 55° C. prior to the addition of 5 ml of the 100× stock solution of ethyl-4-hydroxy-3-methoxycinnamate (premade by dissolving 1 g of ethyl-4-hydroxy-3-methoxycinnamate in 10 ml ethanol), mixing well, and pouring into plates. *Lactobacillus* strains that produce and secrete ferulate esterase into the media are visualized by a halo ring of clearance on the plates. The presence or absence of halo rings indicates ferulate esterase activity in each colony, and the diameter of each ring in mm indicates the strength of the secreted ferulate esterase activity (see FIG. 1 illustrating sixteen bacterial strains on the plates). Twelve out of the thirty-three different *Lactobacillus* specie strains screened demonstrate visible clearing zone on MRS-EHM plates. The screened bacterium with the best ferulate esterase activity is *L. fermentum* NRRL B-1932. The other eleven strains, in order second highest activity to eleventh highest activity, are *L. amylovorus* NRRL B-4540; *L. johnsonii* NRRL B-2178; *L. fermentum* NRRL B-1840; *L. reuteri* NRRL B-14172, *L. mucosae* NRRL B-41068; *L. fermentum* NRRL B-3693; *L. casei* CRL 686; *L. casei* NRRL B-1922; *L. amylophilis* NRRL B-4437; *L. casei* ATTC 4646; and *L. crisptus* NRRL B-4391. See Table 2, supra.

Example 2

Identification of DNA and Amino Acid Sequence of Ferulate Esterase Gene/Protein in *Lactobacillus Fermentum* NRRL B-1932

Using a published sequence of an ethyl ferulate-hydrolyzing esterase gene (GenBank AY837784.1) from *Burkholderia multivorans* (Rashamuse, et al. (2007)) as query sequence, the draft genome of *L. fermentum* IFO 3956 (Morita, et al., *DNA Research* 15(3):151-161 (2008), (GI: 184154476)) is searched, and one hypothetical protein, LAF_1318 (GI: 184155794, YP_001844134), is identified as a putative ferulate esterase. But the genome of *L. fermentum* IFO 3956 (completed December 2014) was incomplete at the time of the project, therefore, the genome of *L. fermentum* CECT5716 is searched (CP002033) using LAF_1318 DNA sequence, and the *L. fermentum* CECT5716 ferulate esterase gene plus flanking regions at both 5' and 3' end of the gene is identified (SEQ ID NO: 1). The putative coding sequence of the *L. fermentum* CECT5716 ferulate esterase gene is in SEQ ID NO: 2. Using bioinformatics analyses tools (SDSC Biology Workbench, San Diego State University, San Diego, Calif.), specific PCR primers Fumpcr 661 (SEQ ID NO: 3: forward primer) and Fumpcr 1531 (SEQ ID NO: 4; reverse primer) are designed based on the *L. fermentum* CECT 5716 gene sequences to amplify the gene and flanking regions of the ferulate esterase gene from *L. fermentum* NRRL B-1932 genomic DNA. The sequence of Fumpcr 611 (forward primer) and Fumpcr 1531 (reverse primer) are contained within SEQ ID NO: 1, upstream and downstream of the putative coding sequence of the ferulate esterase gene, respectively. An approximately 870 bp PCR fragment is generated by PCR using *L. fermentum* NRRL B-1932 genomic DNA and the Fumpcr 611 and Fumpcr 1531 primers. The 870 bp fragment is purified using Qiagen's PCR purification kit (Valencia, Calif.) and cloned into pCR 2.1 cloning vector following manufacturer's instruction (Invitrogen, Carlsbad, Calif.), and a positive clone is selected by colony PCR *E. coli* Dh5 α cells (Invitrogen, Carlsbad, Calif.) are transformed with the purified pCR 2.1 plasmid containing the 870 bp fragment and cultured overnight. Plasmid DNA isolation from *E. coli* is carried out by using QIAprep miniprep kit (Qiagen, Valencia, Calif.). Sequencing of the pCR 2.1 plasmid DNA is done via the ABI Prism 310 using the Dye Terminator Cycle Sequencing Kit (Applied Biosystems, Foster City, Calif.) and analyzed using the SDSC Biology WorkBench (sdsc.edu/Research/biology) to confirms that the 870 bp DNA fragment is the desired ferulate esterase gene from *L. fermentum* NRRL B-1932, which encodes a protein containing 249 amino acids, with a calculated molecular weight of 27.1 kDa. The amino acid sequence of *L. fermentum* NRRL B-1932 ferulate esterase is in SEQ ID NO: 5. The polynucleotide sequence of *L. fermentum* NRRL B-1932 ferulate esterase is SEQ ID NO: 6. The polynucleotide sequences of ferulate esterase from *L. fermentum* CECT 5716 (the coding sequence of SEQ ID NO: 1) and *L. fermentum* NRRL B-1932 (SEQ ID NO: 6) differ by six nucleotides.

Next, a protein sequence search using the protein sequence of LAF_1318 via IMG website (img.jgi.doe.gov/cgi-bin/w/main.cgi) against the genome of *L. fermentum* ATCC-14931, results in the identification of the ferulate esterase protein sequence of *L. fermentum* ATCC-14931, which is given a description of alpha/beta fold family hydrolase. The amino acid sequence of this protein is in SEQ ID NO: 7. This ferulate esterase enzyme has 249 amino acids and a predicted molecular weight of 27.1 kD.

FIG. 2 shows the amino acid sequence alignment of three known ferulate esterase proteins from *L. fermentum* NRRL B-1932 (as described herein)(SEQ ID NO: 5), *L. fermentum* ATCC-14931 (ZP_03945661)(SEQ ID NO: 7) and *L. fermentum* 3956FU (YP_001844134) (SEQ ID NO: 8). Non-identical amino acids are indicated in bold text at amino acids 20, 74, 144, and 193 based on the sequence of ferulate esterase from *L. fermentum* NRRL B-1932.

Example 3

Recombinant Ferulate Esterase Expression and Activity

Based on the cloned ferulate esterase gene in pCR 2.1 vector (described above), two specific primers Fumfae NcoI5' (forward primer SEQ ID NO: 9) and Fumfae BamHI3' (reverse primer SEQ ID NO: 10) are designed to introduce NcoI and BamHI restriction sites at the ends of the ferulate esterase nucleotide sequence by PCR using the cloned ferulate esterase in pCR2.1 as template. The nucleotide sequence of ferulate esterase of *L. fermentum* NRRL B-1932 (SEQ ID NO: 6) is cloned into the expression vector pET28b (Novagen, Billerica, Mass.) at NcoI/BamHI sites.

The nucleotide sequence of the recombinant ferulate esterase protein of *L. fermentum* NRRL B-1392 is cloned into pET28b which is designed for over-expression of the heterologous ferulate esterase protein by IPTG induction. The IPTG-inducible promoter in the pET28b vector is operably linked to the ferulate esterase nucleotide sequence, and the start codon of the ferulate esterase sequence aligns with the NcoI site immediately after the ribosomal binding site sequences in the vector. Based on DNA sequence data, the cloned gene produces a recombinant ferulate esterase from *L. fermentum* NRRL B-1932 containing total of 271 amino acids including the above mentioned 249 amino acids (SEQ ID NO: 5) plus the following 22 residues: RDPNSSSVDK-LAAALEHHHHHH (SEQ ID NO: 11) (sixteen additional amino acids sequences from the vector (linker sequence) and 6 His amino acids (6×HIS tag)) with an estimated molecular weight of 29.6 kDa. The amino acid of the recombinant ferulate esterase containing the linker sequence and 6×HIS tag is in SEQ ID NO: 12. The cDNA of this chimeric ferulate esterase gene with pET28b linker sequence and the 6×HIS tag is in SEQ ID NO: 13. This pET28b plasmid containing DNA encoding the ferulate esterase gene from *L. fermentum* NRRL B-1932 plus the 16 amino acid linker plus the 6×HIS tag (SEQ ID NO: 13) operably linked to IPTG inducible promoter is referred to as pET28bFAE.

Figure 3:
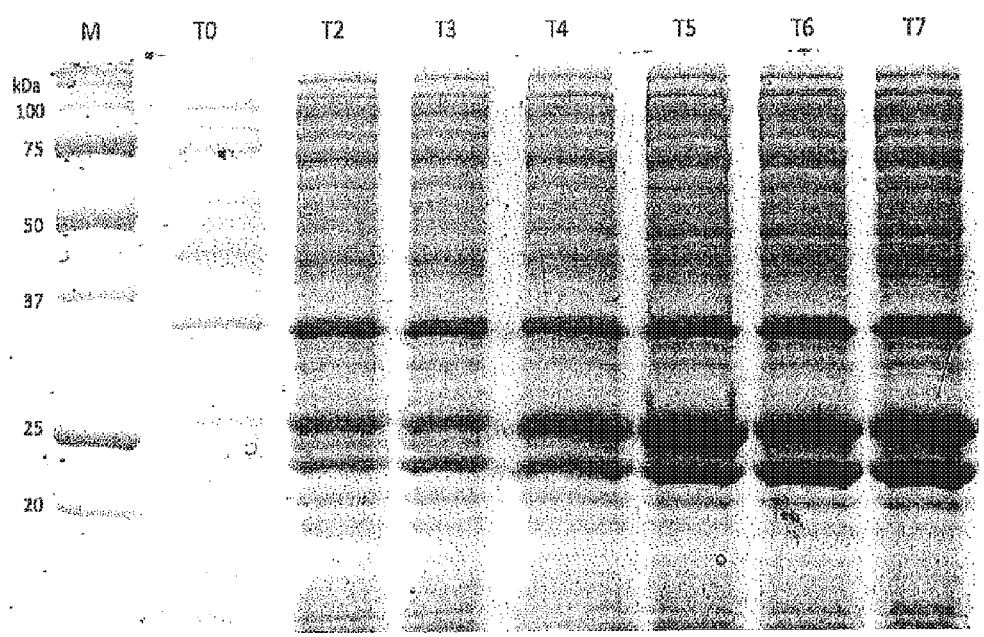
FIG. 3 shows the SDS PAGE analyses of total cellular proteins extracted from recombinant *E. coli* containing an expression vector which has the DNA sequence of ferulate esterase operably linked to an IPTG-inducible promoter (*E. coli* BL21pLysSFAE). The total cellular proteins are collected at 0 (lane TO), 2 (lane T2), 3 (lane T3), 4 (lane T4), 5 (lane T5), 6 (lane T6), and 7 (lane T7) hours after IPTG induction. Lane M contains standardized markers.

Transformation competent *E. coli* BL21pLysS cells are obtained from Life Technologies (Carlsbad, Calif.) and are transformed with pET28bFAE according to manufacturer's suggested protocol. The recombinant *E. coli* BL21pLysSFAE cells are streaked onto LB kan/chlor plate (containing 30.5 μg/ml kanamycin (kan) and 34 μg/ml chloramphenicol (chlor)) and allowed to grow overnight at 37° C. A single colony is inoculated in 3 ml LB kan/chlor and grown at 37° C. at 225 rpm overnight. Then 200 μl of the overnight culture is inoculated into 12 ml LB kan/chlor (30.5 μg/ml kan and 34 μg/ml chlor) and grown at 37° C. at 225 rpm until $OD_{600}$ 0.4-0.6 is achieved. Sufficient IPTG to achieve a final concentration 1 mM IPTG is added to media for transcription induction. Total cellular proteins are extracted from the recombinant E. coli BL21(DE3)pLysSFAE cells collected at different time points after IPTG induction. At the time points indicated below, two 1.5 ml cultures are harvested and centrifuged at 8000 rpm for 5 minutes to pellet the cells. After decanting the liquid, the E. coli BL21(DE3)pLysSFAE cell pellet is lysed with 100 µl lysis solution containing 1 ml B-PER (Bacterial Protein Extraction Reagent, ThermoFischer Scientific, Waltham, Mass.), 2 µl DNase I (2500 U/mL), 2 µl lysozyme (50 mg/mL) in 1.7 ml microcentrifuge tube. The cells are lysed for ~15 minutes at room temperature with gentle shaking. Then the supernatant is transferred to a new microcentrifuge tube after removal of cell debris by centrifugation at 13000 rpm for 10 minutes. The supernatant is used to determine protein concentration using mini assay kit (Bio-Rad, Hercules, Calif.) and ferulate esterase activity by HPLC (as described below). Total cellular protein extracts from 0 hour and 2, 3, 4, 5, 6, and 7 hours after IPTG induction are run on an SDS-PAGE. The 29.6 kDa recombinant protein is produced by E. coli BL21pLysSFAE upon IPTG induction. Progressively stronger bands at 29.6 kDa appear at 2, 3, 4, 5, 6, and 7 hours post-induction, indicating strong production of the recombinant protein (see FIG. 3).

The ferulate esterase activity is determined by HPLC analysis, using a modification of the protocol described inAndersen, et al., *Colloids and Surfaces B: Biointerfaces* 26:47-55 (2002). The specific modifications are described below. First, the substrate stock solutions are prepared in concentrations ranging from 0.05 mM to 6 mM of ethyl ferulate containing 20 µl ethanol, 20 dimethylformamide, and 1.46 ml 100 mM sodium phosphate buffer at pH 6.5. Then for ferulate esterase enzyme reaction, duplicate samples are set up with 100 µl substrate stock solution equilibrated to 37° C., and the reaction is initiated by addition of 2-20 µl purified or crude enzyme solution. Reactions are incubated for 30 minutes at 37° C., and the reactions are stopped by addition of 100 µl MeCN, then the duplicate samples are subjected to HPLC analyses. The incubation mixture is transferred to HPLC vials to detect ferulic acid produced by enzymatic hydrolysis of ethyl ferulate. The samples are applied on HPLC system (Agilent 1100 series, Agilent Technologies, Santa Clara, Calif.), with a UV detector (310 nm) and an Econosphere C18 column (5 µm, 250×4.6 mm (Alltech, Deerfield, Ill.)). A flow rate of 0.8 ml/minute with gradient of increased acetic acid and decreased methanol are used (Table 3). Samples are run at ambient temperature and products are eluted with acidified methanol. Under this condition, ferulic acid is eluted at 11.270 minutes, methyl ferulate at 15.713 minutes and ethyl ferulate at 17.855 minutes.

TABLE 3

| Time | 5% MeOH 0.25% Acetic Acid in H$_2$O | 0.25% Acetic Acid in MeOH |
| --- | --- | --- |
| 0 | 100 | 0 |
| 15 | 50 | 50 |
| 17 | 0 | 100 |
| 20 | 100 | 0 |
| 25 | 100 | 0 |

To quantify ferulic acid, a standard curve of ferulic acid from 0.1 mM to 5 mM is prepared, applied to the HPLC, and the concentration of ferulic acid is calculated for comparison. The enzyme activity is expressed in units, where one unit of ferulate esterase activity is defined as the amount of enzyme required to release 1 µM ferulic acid per minute from ethyl ferulate (1 U=1 µmol/min) in the condition described above. Then, the specific activity is defined as 1 U ferulic acid released per mg of protein used and expressed as mU/mg, as presented in Table 4 below. These results suggest that the recombinant FAE activities reaches the highest levels after 6 hours of IPTG induction.

TABLE 4

| Time (hr) after IPTG induction | T0 | T2 | T3 | T4 | T5 | T6 | T7 |
| --- | --- | --- | --- | --- | --- | --- | --- |
| FAE (mU/mg) | 3.81 | 13.85 | 34.57 | 31.44 | 29.89 | 45.89 | 30.22 |

To test the growth temperature for optimal production of recombinant ferulate esterase in E. coli BL21, recombinant E. coli BL21pLysSFAE cells are grown in LB kan media in 30 ml flasks at 25° C., 32° C., and 37° C. About 3 ml of the cultures are removed and cells are collected by centrifugation after 3 hours of IPTG induction as described above. Total cellular proteins (referred to as "crude ferulate esterase") are extracted using the B-PER kit as described above. Crude ferulate esterase as well as NiNTA purified ferulate esterase (using the protocol described below) from each temperature culture is then run on SDS-PAGE. The lane containing ferulate esterase obtained from the recombinant E. coli incubated at 37° C. has the largest band at approximately 29.6 kDa, thus the recombinant E. coli produce more ferulate esterase protein at 37° C. than the other tested temperatures. Despite more ferulate esterase protein being produced at 37° C., the specific enzymatic activity is highest from bacterial cells cultured at 32° C., see Table 5. Not wishing to be bound to any particular hypothesis, it is speculated that when culturing and inducing transcription of recombinant E. coli BL21pLysSFAE at 32° C., more active ferulate esterases are produced than when culturing the bacteria and inducing transcription at 37° C. which results in some ferulate esterase produced in non-active form.

TABLE 5

| Temperature | 25° C. + IPTG | 32° C. + IPTG | 37° C. + IPTG | 37° C. (no IPTG) |
| --- | --- | --- | --- | --- |
| FAE (mU/mg) | 23.04 | 39.52 | 36.75 | 3.01 |

Example 4

Purification of Recombinant 6-HIS Tagged Ferulate Esterase

The recombinant ferulate esterase is purified using the HIS tag sequence from the expression vector. About 190 µl NiNTA agarose (Qiagen, Germantown, Md.) is added to 500 µl crude cellular total protein extract supernatant described above. The mixture is incubated at 4° C. by shaking at 25 rpm for 1 hour, then loaded onto gravity column. The NiNTA agarose with bound protein is washed 3 times with 1.5 ml NiNTA wash buffer (50 mM NaH$_2$PO$_4$, 300 mM NaCl, 20 mM imidizole) (Qiagen, Germantown, Md.). Proteins are eluted with 2 ml NiNTA elution buffer (50 mM NaH$_2$PO$_4$, 300 mM NaCl, 250 mM imidizole) (Qiagen, Germantown, Md.). The elution fractions are collected and subjected to SDS-PAGE analyses. The protein concentrations are determined by using Bio-Rad protein assay (Hercules, Calif.) according to the manufacture's suggested protocol. The crude recombinant ferulate esterase and the purified recombinant ferulate esterase elution fractions from *E. coli* are analyzed by SDS-PAGE. The recombinant NiNTA purified ferulic acid esterase (50 μl) is added to 20 μl 2×SDS sample buffer and heated 92° C. for 2 minutes. A Mini-Protean TGX 4-15 SDS-PAGE gradient gel (BioRAD, Hercules, Calif.) is run with duplicated loading of 20 μl of the protein sample next to the Precision Plus stained ladder (BioRAD, Hercules, Calif.). The gel is split into two, and one piece is subjected to Coomassie staining following standard protocol; and the other duplicate piece is subjected to zymogram analysis as described below. The gel pieces are washed for 1 hour in 100 mM $KH_2PO_4$ buffer at pH 6, followed by 30 minutes wash in dd$H_2O$. The washed gel is stained with a solution containing 100 μl of 40 mg/ml MUTMAC [4-methylumbelliferoyl (p-trimethylammonium cinnamate chloride)] stock solution in 8 ml of 50 mM $KH_2PO_4$ buffer at pH 6. The zymogram is imaged under UV light with Kodak GelLogic 100 imaging system (Rochester, N.Y.). The zymogram analysis of the purified enzyme from fraction E2 confirms that the ferulate esterase activity corresponds to the approximate position of the recombinant protein on SDS PAGE. The purified ferulate esterase shows strong activities against substrates p-nitrophenyl acetate and 4-methylumbelliferyl (p-trimethylammoniocinnamate chloride).

Figure 4A:
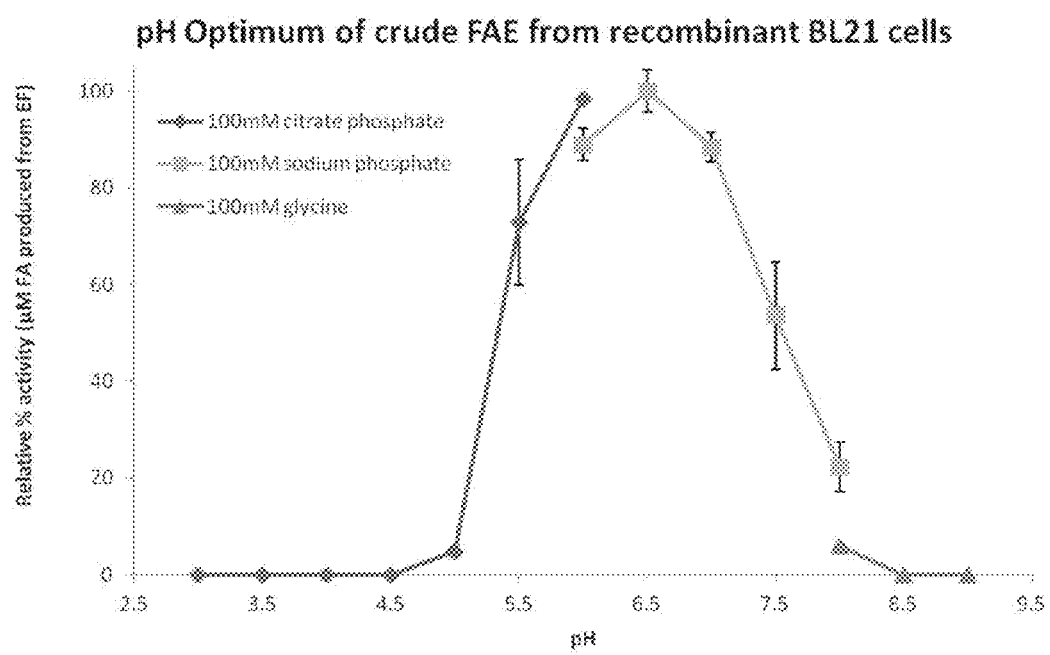
FIG. 4A shows, at a range of pHs, the enzymatic activity of a crude extract of ferulate esterase produced by recombinant *E. coli* BL21pLysSFAE cells (the chimeric protein).
Figure 4B:
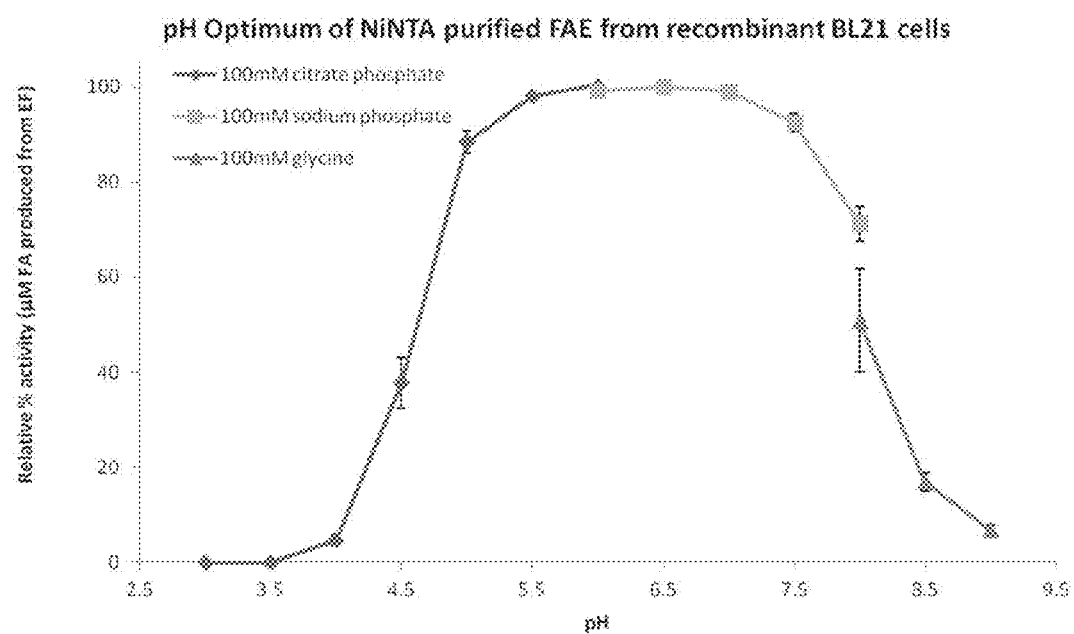
FIG. 4B shows, at a range of pHs, the enzymatic activity of purified ferulate esterase produced by recombinant *E. coli* BL21pLysSFAE cells (the chimeric protein).
Figure 5:
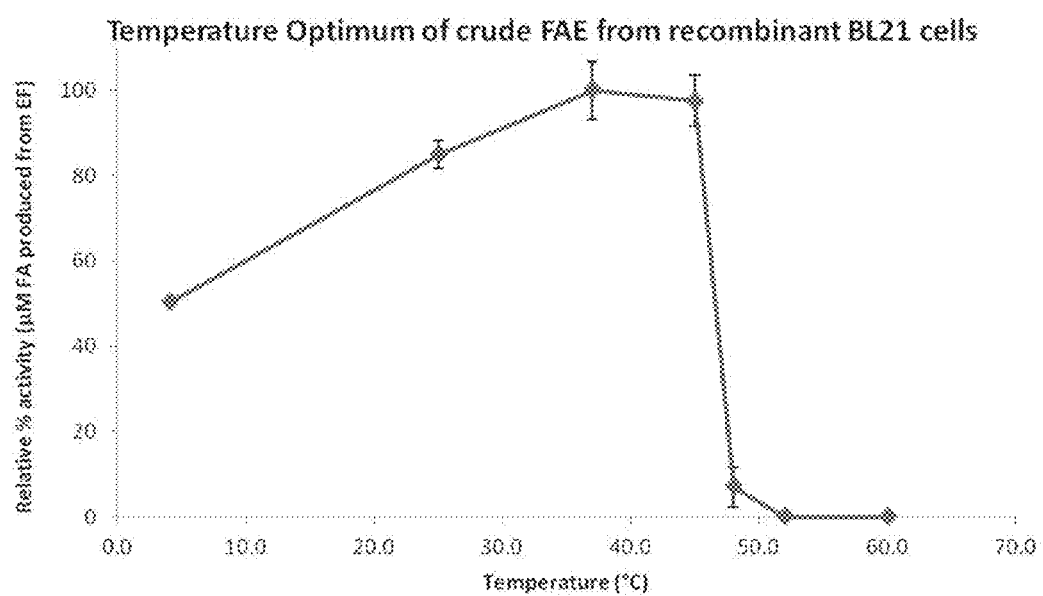
FIG. 5 shows, at a range of temperatures, the enzymatic activity of purified chimeric protein having ferulate esterase activity produced by recombinant *E. coli* BL21pLysSFAE cells.

The optimum pH values for ferulate esterase activity of crude recombinant ferulate esterase and purified recombinant ferulate esterase are determined by using three different reaction buffers; 100 mM citrate phosphate, 100 mM sodium phosphate, and 100 mM glycine. Ferulate esterase activity is determined by HPLC protocols described above, and the results are showed in FIG. 4A and FIG. 4B, respectively. FIG. 4A shows the enzymatic activity of a crude extract of recombinant ferulate esterase at pH ranging from pH 3.0 to pH 9.0 in the three different reaction buffers. FIG. 4B shows the enzymatic activity of purified recombinant ferulate esterase at pH ranging from pH 3.0 to pH 9.0 in the three different reaction buffers. Both the crude recombinant ferulate esterase and purified recombinant ferulate esterase are most active at pH 6.5. The enzymatic activity of the crude recombinant ferulate esterase is assessed at temperatures ranging from 5° C. to 60° C. (5° C., 25° C., 37° C., 45° C., 47° C., 53° C. and 60° C.). The optimum temperature for enzymatic activity of ferulate esterase in the crude extract is 37° C. (see FIG. 5). Duplicated samples of 100 μl 0.2676 mM ethyl ferulate in sodium phosphate buffer at pH 6.5 are equilibrated for 10 minutes at the desired temperatures prior to the addition of the chimeric protein. Reactions are initiated by addition of 2 μl crude recombinant ferulate esterase, and then incubated at the desired temperatures for 20 minutes in microtubes. The reactions are stopped by addition of 100 μl MeCN, and then the duplicate sample mixtures are subjected to HPLC analyses. These results are surprising and unexpected because, for the two prior art disclosed cinnamoyl esterases produced by *L. johnsonii*, one cinnamoyl esterase had maximum activity at 20° C. and pH 7.8, and the other cinnamoyl esterase had maximum activity at 30° C. and pH 6.7 (see Lai, et al., *AEM* 75:5018-5024 (2009)). Also, although a *Lactobacillus johnsonii* strain isolated from stool samples of diabetes-resistant rats was described previously as containing ferulate esterase activity (Kin, et al. (2009)), and *Lactobacillus johnsonii* NRRL B-2178 was demonstrated to have ferulate esterase activity, those enzymatic activities are lower than ferulate esterase activity obtained from *Lactobacillus fermentum* NRRL B-1932. This higher activity is surprising and unexpected.

Although this invention is been exemplified for purposes of illustration and description by reference to certain specific embodiments, it will be apparent to those skilled in the art that various modifications, alterations, and equivalents of the illustrated examples are possible. Any such changes, which derive directly from the teachings herein or do not depart from the spirit and scope of the invention, are deemed to be covered by this invention.

I claim:

1. An expression vector comprising a heterologous polynucleotide operably linked to a promoter wherein said heterologous polynucleotide encodes the DNA sequence of *Lactobacillus fermentum* NRRL B-1932 ferulate esterase and has the sequence of SEQ ID NO: 6.

2. A recombinant bacterium comprising the expression vector of claim 1.

3. An expression vector comprising a heterologous polynucleotide operably linked to a promoter wherein said heterologous polynucleotide encodes the amino acid sequence of *Lactobacillus fermentum* NRRL B-1932 ferulate esterase in SEQ ID NO: 5.

4. A recombinant bacterium comprising the expression vector of claim 3 wherein said recombinant bacterium is not *Lactobacillus fermentum* NRRL B-1932.

5. A chimeric protein comprising a first section having ferulate esterase activity, a second section for purification of said chimeric protein, and optionally a third section for separating said first section from said second section; wherein said first section has the amino acid sequence in SEQ ID NO: 5, wherein said second section for purification comprises a tag, and wherein said optional third section comprising a linker.

6. An expression vector comprising a promoter and a DNA sequence encoding the chimeric protein of claim 5, wherein said promoter is operably linked to said DNA sequence encoding said chimeric protein.

7. A recombinant bacterium comprising the expression vector of claim 6.

8. A chimeric protein comprising a first section having ferulate esterase activity, a second section for purification of said chimeric protein, and a third section for separating said first section from said second section; wherein said chimeric protein has the amino acid sequence of SEQ ID NO: 12.

9. A polynucleotide comprising a DNA sequence encoding the chimeric protein of claim 8.

10. An expression vector comprising the polynucleotide of claim 9, wherein said polynucleotide is operably linked to a promoter in said expression vector.

11. A recombinant bacterium comprising the expression vector of claim 10.

* * * * *